United States Patent [19]

Scherm

[11] 4,273,774

[45] Jun. 16, 1981

[54] CENTRAL NERVOUS SYSTEM COMPOSITIONS AND METHOD

[75] Inventor: Arthur Scherm, Bad Homburg, Fed. Rep. of Germany

[73] Assignee: Merz & Co., Frankfurt, Fed. Rep. of Germany

[21] Appl. No.: 105,419

[22] Filed: Dec. 19, 1979

[30] Foreign Application Priority Data

Dec. 27, 1978 [DE] Fed. Rep. of Germany ....... 2856393

[51] Int. Cl.$^3$ .................... A61K 31/52; A61K 31/135
[52] U.S. Cl. ...................................... 424/253; 424/330
[58] Field of Search ............................... 424/330, 253

[56] References Cited

U.S. PATENT DOCUMENTS

| 3,864,489 | 2/1975 | Biscardi | 424/253 |
| 3,961,060 | 6/1976 | Fuxe | 424/253 |
| 4,122,193 | 10/1978 | Sherm et al. | 424/330 |

Primary Examiner—Stanley J. Friedman

Attorney, Agent, or Firm—Gordon W. Hueschen

[57] ABSTRACT

The present application relates to compositions which influence the central nervous system and which are especially useful in the treatment of hyperkinesis and rigidity. These compositions contain as active ingredient 1,3-dimethyl-5-aminoadamantane in the form of the free base or a pharmaceutically-acceptable salt thereof, together with a methylxanthine compound, e.g., caffeine or theophylline, in an amount up to about fifteen milligrams of the methylxanthine compound per each milligram of the 1,3-dimethyl-5-aminoadamantane compound. These compositions are useful in the treatment of central nervous system disorders, particularly of Parkinson's disease, depressions, spasticity, rigidity, hyperkinesis, and the like. The compositions possess unpredictable beneficial properties of a synergistic nature. The application also relates to the treatment of such central nervous system ailments or conditions with a combination of the said two active agents either concurrently or together in the same dosage form or unit.

11 Claims, 1 Drawing Figure

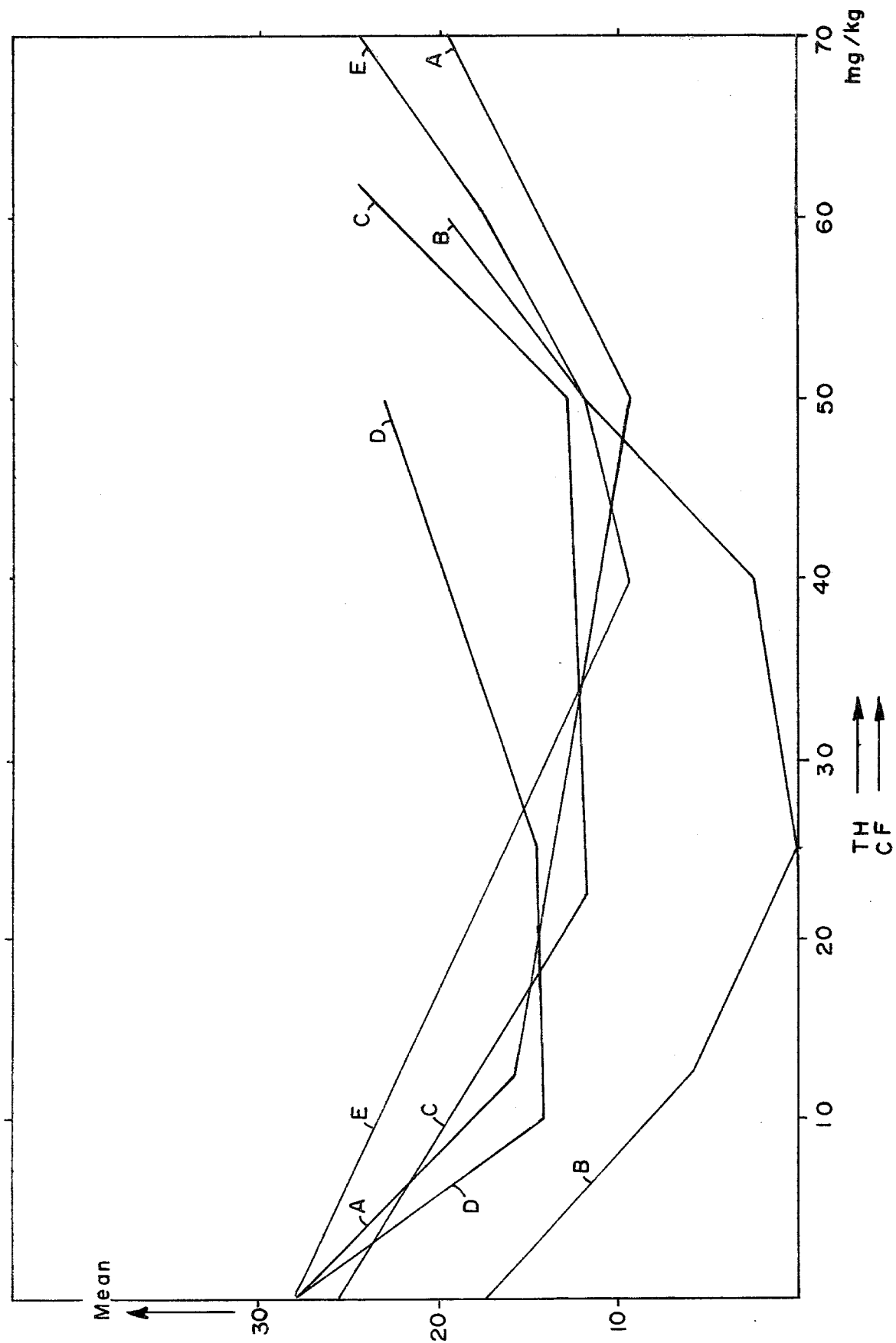

CENTRAL NERVOUS SYSTEM COMPOSITIONS AND METHOD

BACKGROUND OF THE INVENTION

1. Field of Invention

Dopaminergic, anticataleptic central nervous system compositions useful in the treatment of central nervous system ailments and disorders, particularly Parkison's disease, depressions, spasticity, hyperkinesis, and rigidity. Treatment of such central nervous system disorders or ailments with combination therapy including a 1,3-dimethyl-5-aminodamantane compound.

2. Prior Art

In the past, numerous proposals have been made for drugs which influence the central nervous system and are useful for the treatment of ailments or disorders thereof, particularly including Parkinson's disease, depressions, spasticity, hyperkinesis, rigidity, and the like. At present, such treatment is predominantly carried out with the employment of three separate therapeutically active agents, having different modes of action and having widely different structures. These products are L-dopa, aminoadamantanes, and anticholinergics. Dependent on the form and intensity of the disease involved, rigor, tremor, and bradyphrenia are the target of the treatment. In many cases, however, single doses of 200 to 300 milligrams of the active agent are necessary to achieve a satisfactory effect on rigidity, but such dosages are already regarded as undesirably pathological. Such drugs act on akinesia and rigidity, but a wide range of effects, including also desirable reduction of tremor and treatment of bradyphrenia, can in most cases only be effected through the employment of greatly increased dosages. It is therefore obviously necessary to provide new active ingredients or agents or combinations thereof, whereby the desirable effects can be accomplished without the undesirable and even pathological increase in dosage. It is therefore highly desirable to provide combinations of active agents which potentiate each other, or in which one potentiates the activity of the other, both of which active agents are preferably already known and established in therapy. At the same time, any such combination should present, if at all possible, an improved therapeutic ratio and diminished side effects. This is sometimes possible when the potentiating effect of the one active ingredient upon the other is sufficient to permit a significant reduction in dosage.

Among the substances previously proposed for influencing the central nervous system and as especially useful in the treatment of hyperkinesis and rigidity, and particularly in the treatment of Parkinson's disease, is the compound 1,3-dimethyl-5-aminoadamantane or a pharmaceutically-acceptable salt thereof, which acts upon rigor, tremor, and akinesia. Animal experiments have revealed the anticataleptic and locomotor activity of this compound at doses of five through twenty milligrams per kilogram of body weight.

Many recent publications have dealt with the range of activity of 1,3-dimethyl-5-aminoadamantane and its pharmaceutically-acceptable salts, e.g.:

Drugs of the Future Vol. I, No. 9 (1976), 427 ff; Arzneimittel-Forschung "Drug Research" 27 (II), No. 7 (1977), 1477–1487 ff; European Journal of Pharmacology 26 (1974), 9–14, North-Holland Publishing Company; Arzneimittel-Forschung "Drug Research" 23, No. 12 (1973), 1737–1739. See also U.S. Pat. No. 4,122,193, issued Oct. 24, 1978, claiming compositions of 1,3-dimethyl-5-aminoadamantane and pharmaceutically-acceptable salts thereof and a method of treating hyperkinesis therewith.

The second active ingredient, which also plays an important part in the unpredictable effectiveness of the new combinations and method of the present invention, is a methylxanthine compound, e.g., caffeine or theophylline, both of which are old and well-known in the art and the therapeutic action of which is sufficiently described in the literature.

With regard to the prior art concerning potentiation of dopaminergic activity by means of drug combinations and combination therapy, reference is made herein to German OL No. 2518677, filed Apr. 26, 1975, and laid open on Nov. 20, 1975, which discloses dopaminergic stimulating compositions comprising certain alkaloids together with phosphodiesterase inhibitors. Although caffeine and theophyllamine are reported to be phosphodiesterase inhibitors, any potentiation which might result from a combination thereof with certain alkaloids certainly is no teaching or suggestion that they might be used to potentiate the activity of 1,3-dimethyl-5-aminoadamantane or a pharmaceutically-acceptable salt thereof, which indeed possess a far different chemical structure and activity than the alkaloids of the German OL.

As far as combination therapy, reference is also made to U.S. Pat. No. 3,961,060, issued June 1, 1976, wherein a phosphodiesterase inhibitor such as caffeine is combined with dopa, m-tyrosine, apomorphine, or a compound designated ET495, for purposes of allegedly potentiating dopaminergic effect. All the compounds disclosed in that patent, the dopaminergic activity of which is allegedly potentiated, have structures far different than the 1,3-dimethyl-5-aminoadamantane employed in the compositions and method of the present invention, and of course are also presumed to operate along entirely different metabolic pathways. Further, the evidence apparently presented in the U.S. Pat. No. 3,961,060 appears to be limited to potentiation of the dopaminergic effect of dopa itself by caffeine, which of course is hardly any suggestion to combine a methylxanthine such as caffeine or theophylline with a compound such as 1,3-dimethyl-5-aminoadamantane or a pharmaceutically-acceptable salt thereof, inasmuch as such compound contains three (3) rings compared to the single ring in dopa, as well as three (3) less functional groups than dopa, much less that caffeine or theophylline or any methylxanthine compound would in fact serve to potentiate the highly desirable activity of 1,3-dimethyl-5-aminoadamantane or a pharmaceutically-acceptable salt thereof, particularly with respect to what is undoubtedly the most important result of such combination therapy, namely, reduction in rigidity.

Accordingly, in the compositions of the present invention and according to the method of the present invention, the methylxanthine compound such as caffeine or theophylline unpredictably, and to an unpredictable and highly desirable extent, potentiates the activity of the 1,3-dimethyl-5-aminoadamantane or pharmaceutically-acceptable salt thereof and provides another important addition to the physician's armamentarium of useful drugs in this area.

SUMMARY OF THE INVENTION

The present application relates to compositions which influence the central nervous system and which are especially useful in the treatment of hyperkinesis and rigidity. These compositions contain as active ingredient a 1,3-dimethyl-5-aminoadamantane in the form of the free base or a pharmaceutically-acceptable salt thereof, together with a methylxanthine compound, e.g., caffeine or theophylline, in an amount up to about fifteen milligrams of the methylxanthine compound per each milligram of the 1,3-dimethyl-5-aminoadamantane compound. These compositions are useful in the treatment of central nervous system disorders, particularly of Parkinson's disease, depressions, spasticity, rigidity, hyperkinesis, and the like. The compositions possess unpredictable beneficial properties of a synergistic nature. The application also relates to the treatment of such central nervous system ailments or conditions with a combination of the said two active agents either concurrently or together in the same dosage unit to produce unprecedented and unpredictable results, including the highly desirable but difficultly-attained diminution of rigidity. Preferably the active ingredient is up to about ten milligrams of the 1,3-dimethyl-5-aminoadamantane compound, especially up to about five milligrams of the 1,3-dimethyl-5-aminoadamantane compound, where such lower dosage are adequate, and preferably the combined therapy is administered orally or parenterally in dosage unit form, generally with a conventional pharmaceutically-acceptable carrier also being present in the pharmaceutical form administered.

It has now unexpectedly been found that, by the administration of a combination of 1,3-dimethyl-5-aminoadamantane, having the following formula:

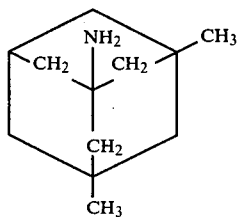

or a pharmaceutically-acceptable salt thereof (A) and a methylxanthine, e.g. caffeine or theophylline, having the following formulas:

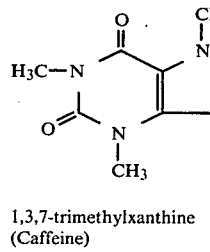 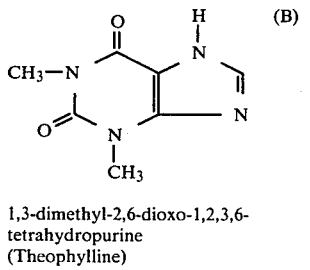

1,3,7-trimethylxanthine (Caffeine)

1,3-dimethyl-2,6-dioxo-1,2,3,6-tetrahydropurine (Theophylline)

the respective dosage of B being up to fifteen (15) parts or milligrams per part or milligram of A, it is now possible:

(a) to maintain the dosage necessary to produce a certain action or effect upon rigidity at a lower level than has previously been possible with administration of A only;

(b) to achieve a stronger effect upon rigidity at a given dosage of the substance than with the administration of A alone; and, importantly, (c) to reduce the side-effects and thereby produce a more favorable therapeutic ratio than previously attainable.

OBJECTS OF THE INVENTION

It is an object of the present invention to provide valuable compositions influencing the central nervous system of the type just described, having advantageous and unpredictable properties which make them especially useful in the treatment of hyperkinesis and rigidity. It is another object of the invention to provide a method of combination therapy involving the concurrent treatment with the two active ingredients involved, as aforementioned, preferably in the form of a single dosage unit. Other objects of the invention will become apparent hereinafter, and still others will be obvious to one skilled in the art.

THE DRAWING

Reference is now made to the drawing, wherein the single FIGURE is a graph comprising several curves A-E. In the FIGURE, the abscissa represents the amount of the methylxanthine employed in mg/kg whereas the ordinate represents the mean degree of rigidity. The curves in the FIGURE correspond to the pharmacological data presented herein under "PHARMACOLOGY", the variations in the numbers on the abscissa and on the ordinate being obtained upon administration of constant dosages of the 1,3-dimethyl-5-aminoadmantane compound and upon variation of the dosage of the methylxanthine compound.

PHARMACOLOGY

The effectiveness of the new combination of A and B is based on the following synergistic effect:

When given separately, caffeine and theophylline have no effect on rigidity as can be taken from the curves. A combination of A (up to 10 mg) and B (up to 70 mg), however, has a marked effect on rigidty. Upon administration of a combination of A and B, the following synergistic effects can be demonstrated on a model, within a ratio of up to 15 parts of B per 1 part of A.

1. A acts on rigidity, whereas B does not act on rigidity at all. The administration of a combination of A and B, however, brings about a significant effect upon rigidity which is markedly stronger than the effect of A alone.

2. Upon administration of a combination of both substances, low doses of B are already sufficient to intensify the antiparkinsonian effect of A. This potentiating effect is markedly stronger than the effect of A alone. This action can be demonstrated by all model experiments carried out.

The effect of the combination of A and B will be explained by the following pharmacological examples:

(a) Decrease of rigidity by the combination of A and B in experimentally-induced catalepsy.

The tests were carried out on male Wistar rats receiving food ad libitum. Catalepsy was induced by administration of Spiroperidol according to the well-known, accepted, and published method of Delini-Stula and Merpurgo, and was examined every thirty (30) minutes during a period of 2½ hours. According to standard procedure, before injecting 1,3-dimethyl-5-aminoadamantane, a peripheral decarboxylase inhibitor (R0-4-4602) was also administered. The combinations of A and B, in the doses set forth in the table, were administered to the animals for ten days by the peroral route. The results are summarized in the following tables.

A dosage of B in the combination of A and B has a stronger rigor-reducing effect than a single dose of compound A. A dose increase of component B potentiates the action and shows a maximum at 50 mg/kg (Curve A).

According to Curve B, the action of A is still more intensified by combination with 10 mg/kg of theophylline (Component B), resulting in a maximum of rigor-reduction. Similar results can be taken from Curve C.

The effect of theophylline (TH), caffeine (CF), and 1,3-dimethyl-5-aminoadamantane (A) on rats (catalepsy induced by Spiroperidol):

|  | Test No. | Substance and Dosage (mg/kg) | Mean ± | Standard error of the mean (s.e.m.) | P |
|---|---|---|---|---|---|
| Curve A | I | A 5 | 28,8 — | 0,8 |  |
|  | II | CF 12,5 + A 5 | 16,3 — | 3,9 |  |
|  | III | CF 25 + A 5 | 13,2 — | 4,5 |  |
|  | IV | CF 50 + A 5 | 9,3 — | 4,6 |  |
|  | V | CF 60 + A 5 | 13,0 |  |  |
|  | VI | CF 70 + A 5 | 19,5 |  |  |
| Curve B | VII | TH 12,5 + A 10 | 5,5 — | 4,6 |  |
|  | VIII | TH 23 + A 10 | 0,7 — | 0,4 |  |
|  | IX | TH 40 + A 10 | 2,5 |  |  |
|  | X | TH 50 + A 10 | 11,8 |  |  |
|  | XI | TH 60 + A 10 | 19,5 |  |  |
| Curve C | XII | TH 0 + A 5 | 25,3 — | 2,2 |  |
|  | XIII | TH 25 + A 5 | 11,5 — | 2,8 |  |
|  | XIV | TH 50 + A 5 | 13,0 |  |  |
|  | XV | TH 60 + A 5 | 22,5 |  |  |

(b) Decrease of rigidity by the combination of A and B in experimentally-induced catalepsy The test was carried out in analogy to (a) with the exception that catalepsy was induced by Reserpine. The results showed that, under the aforementioned test conditions, A did not effect any reduction in rigidity, even at doses of 5 mg/kg.

A combination of A and B, however, brings about a marked decrease in rigidity (Curve D) even at a low dosage of B (10 mg/kg). Upon repeating the test with theophylline, an action maximum could be found at 40 mg/kg theophylline.

The effect of theophylline (TH), caffeine (CF), and 1,3-dimethyl-5-aminoadamantane (A) on rats (catalepsy induced by Reserpine):

|  | Test No. | Substance and Dosage (mg/kg) | Mean ± | Standard error of the mean (s.e.m.) | P |
|---|---|---|---|---|---|
| Curve D | I | CF 0 + A 5 | 28,0 — |  |  |
|  | II | CF 10 + A 5 | 14,0 — |  |  |
|  | III | CF 25 + A 5 | 14,0 — | 4,2 |  |
|  | IV | CF 50 + A 5 | 23,2 — | 1,1 |  |
| Curve E | V | TH 0 + A 5 | 28,0 — | 1,4 |  |
|  | VI | TH 10 + A 5 | 22,7 — | 1,5 |  |
|  | VII | TH 25 + A 5 | 15,3 — | 3,8 |  |
|  | VIII | TH 40 + A 5 | 9,5 |  |  |
|  | IX | TH 50 + A 5 | 12,0 |  |  |
|  | X | TH 60 + A 5 | 17,5 |  |  |
|  | XI | TH 70 + A 5 | 24,5 |  |  |

SPECIFIC EMBODIMENTS OF THE INVENTION

The following examples are given to illustrate specific compositions which may be employed in carrying out the method of the invention and which are representative of the compositions of the present invention, but are not to be construed as limiting.

EXAMPLE 1

Injectible Solutions 1,3-Dimethyl-5-aminoadamantane and theophylline are dissolved in double-distilled water with addition of sodium chloride. Subsequently, the solution is filtered through degerminating layers, filled into two ml ampules and subjected to thermal sterilization for twenty minutes at 120° C.

Injectible solution containing 10 mg of 1,3-dimethyl-5-aminoadamantane and 100 mg of theophylline (10 ml ampule):

| 1,3-Dimethyl-5-aminoadamantane | 0.1 g* |
|---|---|
| Theophylline | 1.0 g |
| Sodium chloride | 0.6 g |
| Double-distilled water | ad 100 ml |

*If the hydrochloride is employed, an equivalent amount of the free base is utilized.

EXAMPLE 2

Solution 1,3-Dimethyl-5-aminoadamantane and theophylline are dissolved in an ethanol-water mixture. The solution is filtered until it remains clear.

Solution containing 5 mg of 1,3-dimethyl-5-aminoadamantane and 30 mg of theophylline per 20 drops=0.5 ml:

| 1,3-Dimethyl-5-aminoadamantane | 1 g* |
|---|---|
| Theophylline | 6 g |
| Ethanol | 10 g |
| Demineralized water | 83 g |
|  | 100 g |

*If the hydrochloride is employed, an equivalent amount of the free base is utilized. The same is true if another salt, e.g., the hydrobromide or sulphate, is employed.

EXAMPLE 3

Tablets

Tablets containing 10 mg of 1,3-dimethyl-5-aminoadamantane and 100 mg of caffeine per tablet of 300 mg:

| 1,3-Dimethyl-5-aminoadamantane | 100 g |
|---|---|
| Caffeine | 1000 g |
| Lactose | 1530 g |
| Polyvinylpyrrolidone | 40 g |
| Polyvinylpyrrolidone solution (10% in isopropanol) | 100 g |
| Potato starch | 250 g |
| Talcum | 49 g |
| Magnesium stearate | 21 g |
|  | 3000 g |

The 1,3-dimethyl-5-aminoadamantane, caffeine, lactose and PVP are mixed and subjected to wet granulation with the PVP solution. After drying, potato starch, talcum and stearate are admixed with the granulate, and tablets of 300 mg compressed.

EXAMPLE 4

Coated Tablets

For the manufacture of coated tablets, tablet cores of 100 or 300 mg are compressed as described in Example 3. These tablet cores are then coated, e.g., according to the sugar-coating procedure: The core is covered with the coating suspension, colored with colored syrup, and polished.

An example for the coating of a 100 or 300 mg tablet core, containing 10 mg of 1,3-dimethyl-5-aminoadamantane and 100 mg of caffeine per core, follows:

| | |
|---|---|
| Core | 100.0 mg |
| Sugar | 65.0 mg |
| Talcum | 39.0 mg |
| Calcium carbonate | 13.0 mg |
| Gum arabic | 6.5 mg |
| Corn starch | 3.7 mg |
| Shellac | 1.1 mg |
| Polyethylene glycol | 0.2 mg |
| Magnesia usta | 1.3 mg |
| Colorant | 0.2 mg |
| | 230.0 mg |

It has accordingly been shown from the foregoing that the subject matter of the present invention is a composition for influencing the central nervous system and which is especially useful in the treatment of hyperkinesis and rigidity, particularly in the treatment of Parkinson's disease, comprising a combination of 1,3-dimethyl-5-aminoadamantane or a pharmaceutically-acceptable acid addition salt thereof, together with at least one methylxanthine compound, such as caffeine or theophylline, wherein the combination therapy or combination composition comprises up to fifteen milligrams or parts of the methylxanthine compound per each milligram or part of 1,3-dimethyl-5-aminoadamantane.

THe compositions made available according to the present invention are especially suitable for use in human medicine, being useful in the treatment of central nervous system ailments and afflictions generally, particularly of Parkinson's disease, depressions, spasticity, rigidity, hyperkinesis, and the like.

According to the present invention, the active ingredients are administered either contemporaneously, simultaneously, or together in a unit dosage form. They may be administered by the oral or parenteral, e.g., intraperitoneal, route. For these purposes, tablets, capsules, solutions, and injectable solutions are particularly suitable. Carrier substances, if desired, may be administered together therewith and the common organic and inorganic adjuvants which do not react with the active ingredients, for example, water, ethanol, polyethylene glycol, gelatine, lactose, starch, magnesium stearate, talcum, cellulose, and the like may be employed for this purpose. If necessary, the formulations may be stabilized and/or sterilized by a mixture with one or more of preservatives, wetting agents, buffers, colors, and essences or flavors. Preparations providing sustained release of the active ingredients may also be provided in known manner. In all of these compositions, the 1,3-dimethyl-5-aminoadamantane compound is either present as the free base or as a pharmaceutically-acceptable salt thereof.

Suitable salts of 1,3-dimethyl-5-aminoadamantane, which can be employed in the compositions and according to the method of the invention, are well known and are the usual amine acid addition salts, either of an organic or inorganic nature, such as the hydrochloride, hydrobromide, sulphate, citrate, tartrate, and the like, as disclosed in the aforesaid U.S. Pat. No. 4,122,193 and elsewhere in the prior art. These salts are made from the free basic compound in known manner according to the skill of the art, and in accord with the aforesaid disclosure of U.S. Pat. No. 4,122,193 and the examples thereof.

Thus, the active ingredient is the free 1,3-dimethyl-5-aminoadamantane base or a pharmaceutically-acceptable salt thereof, numerous of which are disclosed in the aforesaid U.S. Pat. No. 4,122,193.

The method of the invention, accordingly, comprises administering, by any suitable route, preferably orally, to a subject in need thereof, the 1,3-dimethyl-5-aminoadamantane or a pharmaceutically-acceptable salt thereof together with a methylxanthine compound, e.g., caffeine or theophylline, in an amount up to about fifteen milligrams or parts of the methylxanthine compound for each milligram or part of the 1,3-dimethyl-5-aminoadamantane. The administration may be simultaneous, concurrent, or in a single unit dosage form. The compounds may be utilized either per se or preferably in the form of pharmaceutical compositions in admixture together with the usual pharmaceutical diluents, carriers, or adjuvants, according to the customary procedure of the art. They may, in this manner, be embodied into pharmaceutical compositions comprising an effective anti-hyperkinesically effective amount of the combination of active ingredients according to the invention together with the pharmaceutically-acceptable carrier. They may be administered in the form of such pharmaceutical compositions wherein the amount of 1,3-dimethyl-5-aminoadamantane compound is up to give milligrams and, where higher dosages are required, up to ten milligrams, depending upon the patient involved and the exact syndrome being treated, or even greater or lesser amounts, depending of course upon the judgment of the physician in charge, body weight of the patient, degree of central nervous system affliction, etc. The daily regimen is accordingly any number, e.g., 2-4, of such unit dosages as previously mentioned for ameliorative or maintenance treatment of the exact condition involved. When the combination of compounds or compositions of the invention are employed for such purpose, they are administered to a subject in need thereof, particularly a subject suffering from Parkinson's disease, hyperkinesis, and rigidity, but also possibly for the relief of depressions, spasticity, and the like, the amount of the methylxanthine compound being present in an amount up to about fifteen milligrams or parts per each milligram or part of the 1,3-dimethyl-5-aminoadamantane active ingredient, the amount of the two ingredients together constituting an effective anti-hyperkinesically effective amount. As previously stated, the exact amounts and dosage regimens employed will depend upon the patient involved, the exact syndrome being treated, the gravity of the central nervous system affliction, the judgment of the physician in charge, the body weight of the patient, and so on but, as previously indicated, the amount of the 1-amino-3,5-dimethyladamantane, when given in a composition of the present invention or concurrently with the methylxanthine such as caffeine or theophylline, is generally less than the effective anti-hyperkinesic amount of the same compound when given alone, so that the dosages and dosage regiments can be accordingly decreased in practice.

It is to be understood that the invention is not to be limited to the exact details of operation or exact compounds, compositions, methods, or procedures shown and described, as obvious modifications and equivalents will be apparent to one skilled in the art, and the invention is therefore to be limited only by the full scope of the appended claims.

I claim:

1. A composition which influences the central nervous system and is especially useful in the treatment of hyperkinesis and rigidity, which contains the compound 1,3-dimethyl-5-aminoadamantane or a pharmaceutically-acceptable salt thereof, characterized in that it contains a potentiating amount of a methylxanthine compound selected from caffeine and theophylline, the methylxanthine compound being present in said composition in a potentiating amount up to about fifteen milligrams per milligram of the 1,3-dimethyl-5-aminoadamantane.

2. Composition of claim 1 containing up to about ten milligrams of the 1,3-dimethyl-5-aminoadamantane compound.

3. Composition of claim 1 containing up to about five milligrams of the 1,3-dimethyl-5-aminoadamantane compound.

4. A composition of claim 1, adapted to be administered orally or parenterally in dosage unit form.

5. A composition of claim 1, wherein a pharmaceutically-acceptable carrier is also present.

6. A method for influencing the central nervous system which is especially useful in the treatment of hyperkinesis and rigidity, comprising concurrently administering to a host in need of such treatment the compound (a) 1,3-dimethyl-5-aminoadamantane or a pharmaceutically-acceptable salt thereof and (b) a methylxanthine compound, selected from caffeine and theophylline, in an amount up to about fifteen milligrams of the methylxanthine compound per milligram of the 1,3-dimethyl-5-aminoadamantane compound, the combination of (a) and (b) constituting an effective antihyperkinesic dose.

7. A method of claim 6, wherein the treatment is effected by administering a composition of claim 1.

8. A method of claim 6, wherein the treatment is effected by administering a composition of claim 2.

9. A method of claim 6, wherein the treatment is effected by administering a composition of claim 3.

10. A method of claim 6, wherein the treatment is effected by administering a composition of claim 4.

11. A method of claim 6, wherein the treatment is effected by administering a composition of claim 5.

* * * * *

UNITED STATES PATENT AND TRADEMARK OFFICE
CERTIFICATE OF CORRECTION

PATENT NO. : 4,273,774
DATED : June 16, 1981
INVENTOR(S) : Arthur Scherm

It is certified that error appears in the above—identified patent and that said Letters Patent is hereby corrected as shown below:

[56] References Cited, U.S. PATENT DOCUMENTS, line 3; "Sherm et al." should read -- Scherm et al. -- (copy of original Letters Patent)
Col. 1, line 9; "Parkison's" should read -- Parkinson's --
Col. 1, line 13; "-5-aminodamantane" should read -- -5-aminoadamantane --
Col. 4, lines 30 & 31; "-5-aminoadmantane" should read -- -5-aminoadamantane --
Col. 4, line 40; "rigidty" should read -- rigidity --
Col. 5, line 35; insert a period (.) after "catalepsy"
Col. 7, line 38; "THe" (first occurrence) should read -- The --
Col. 8, line 36; "give" should read -- five --

Signed and Sealed this

Sixth Day of October 1981

[SEAL]

*Attest:*

GERALD J. MOSSINGHOFF

*Attesting Officer*        *Commissioner of Patents and Trademarks*